United States Patent [19]

Baird et al.

[11] Patent Number: 5,132,408
[45] Date of Patent: Jul. 21, 1992

[54] FIBROBLAST GROWTH FACTOR ANTAGONISTS

[75] Inventors: Andrew J. Baird; Nicholas C. Ling, both of San Diego, Calif.

[73] Assignee: The Salk Institute for Biological Studies, San Diego, Calif.

[21] Appl. No.: 270,225

[22] Filed: Nov. 14, 1988

[51] Int. Cl.$^5$ ............................ C07K 7/04; C07K 7/06; C07K 7/08; C07K 7/10
[52] U.S. Cl. ..................................... 530/399; 530/324; 530/325; 530/326; 530/327; 530/330
[58] Field of Search ....................... 530/399, 324–330

[56] References Cited

U.S. PATENT DOCUMENTS 4,444,760 4/1984 Thomas, Jr. ............................ 514/21

OTHER PUBLICATIONS

Esch et al., *Proc. Natl. Acad. Sci. USA*, 82, 6507–6511, 1985.

Gaspodarowicz et al., *Biochem. Biophys. Res. Commun.*, 128, No. 2, 554–562 (1985).

Esch et al., *Biochem. Biophys. Res. Commun.*, 133, No. 2, 554–562, 1985.

*Primary Examiner*—F. T. Moezie
*Attorney, Agent, or Firm*—Fitch, Even, Tabin & Flannery

[57] ABSTRACT

Antagonists to basic fibroblast growth factor, a 146 amino acid residue polypeptide, are produced. These antagonists are generally between 4 and 45 residues in length and are characterized by their ability to interact with the FGF receptor and/or inhibit and therefore modulate endothelial and other cell growth. One group of these antagonists includes the four residue sequence which forms basic FGF(36–39), namely Pro-Asp-Gly-Arg. Another of these antagonists includes the sequence of bovine basic FGF(106–115), namely Tyr-Arg-Ser-Arg-Lys-Tyr-Ser-Ser-Trp-Tyr. These peptides are also antagonistic to acidic FGF and other members of the family of FGF peptides. They are effective to combat FGF-promoted mitosis in melanomas and the like.

7 Claims, No Drawings

FIBROBLAST GROWTH FACTOR ANTAGONISTS

This invention was made with Government support under Grant Nos. HD-09690 and AM-18881, awarded by the National Institutes of Health. The Government has certain rights in this invention.

This application is a continuation-in-part of earlier application Ser. No. 854,843, filed Apr. 22, 1986, now abandoned.

The present invention is directed to fibroblast growth factor (FGF) and more particularly to FGF antagonists produced by synthetic methods, which can be used to reduce the effects of mammalian FGF in certain instances.

BACKGROUND OF THE INVENTION

Both the brain and the pituitary gland have been known to contain mitogenic factors for cultured cells; however, until 1974, it was unclear what their relationship was with classical pituitary hormones, such as TSH, LH, FSH, GH and ACTH. In 1974, the purification of a bovine growth factor called basic fibroblast growth factor (bFGF) was reported which was shown to from pituitary hormones, Gospodarowicz, D. *Nature.* 249, 123-127 (1974) This growth factor is now known to have a MW of 16,415, is basic (a pI of 9.6), and is a potent mitogen for either distinct normal diploid fibroblasts or established cell lines. Purification of another growth factor, acidic brain fibroblast growth factor (aFGF) is described in U.S. Pat. No. 4,444,760 (Apr. 24, 1984). Complete characterization of bovine aFGF was reported by Esch et al., *Biochemical and Biophysical Research Communications,* 133, 554-562 (1985).

Later studies confirmed that, in addition to fibroblasts, FGF is also mitogenic for a wide variety of normal diploid mesoderm-derived and neural crest-derived cells including granulosa cells, adrenal cortical cells, chondrocytes, myoblasts, corneal and vascular endothelial cells from either bovine or human origin, vascular smooth muscle cells, the lens epithelial cells. FGF has also been shown to substitute for epithelial cells. FGF has also been shown to substitute for platelet-derived growth factor in its ability to support the proliferation of fibroblasts exposed to plasma-supplemented medium. Consistent with its ability to stimulate the proliferation of bovine and human vascular endothelial cells, FGF has a similar activity in vivo upon capillary endothelial cells; therefore, FGF is considered an angiogenic factor.

SUMMARY OF THE INVENTION

The present invention provides FGF antagonists which may be produced by synthetic methods and which substantially counteract the biological effect of mammalian FGF in certain instances.

The present invention provides antagonists to basic and acidic fibroblast growth factor which may be synthesized using recombinant DNA techniques or other suitable techniques, such as classical or solid phase synthesis. Basic FGF is a 146 amino acid residue polypeptide having the sequence set forth hereinafter. It appears most likely that, in the native bovine FGF molecule, none of the cysteine residues are disulfide-bonded to each other, but that there may be bonding of one or more of the cysteine residues to free cysteine molecules. In any case, the present invention provides biologically active peptides that suppress the biological activity of FGF. They can be synthesized by a recombinant DNA technique or by standard chain elongation procedures involving stepwise addition of amino acid residues, such as solid-phase synthesis upon a solid resin support.

Pharmaceutical compositions in accordance with invention include FGF antagonists or nontoxic salts thereof dispersed in a pharmaceutically acceptable liquid or solid carrier. Such pharmaceutical compositions can be used in clinical medicine, both human and veterinary, and in acute or chronic administration for diagnostic or therapeutic purposes. They are useful both in vivo and in vitro in modulating the growth of endothelial and other related cell types.

DETAILED DESCRIPTION OF CERTAIN PREFERRED EMBODIMENTS

The invention provides antagonists to mammalian FGF, particularly to bovine basic FGF, but also to acidic FGF, which can be readily synthesized. The nomenclature used to define the peptides is that specified by Schroder & Lubke, "The Peptides", Academic Press (1965), wherein in accordance with conventional representation the residue having the free alpha-amino group at the N-terminus appears to left and the residue having the alpha-carboxyl group at the C-terminus to the right. Where the amino acid residue has isomeric forms, it is the L-form of the amino acid that is represented. Bovine basic FGF has been found to be a peptide having the following sequence:

```
                        5                  10                     15
Pro—Ala—Leu—Pro—Glu—Asp—Gly—Gly—Ser—Gly—Ala—Phe—Pro—Pro—Gly—

20                  25                     30
His—Phe—Lys—Asp—Pro—Lys—Arg—Leu—Tyr—Cys—Lys—Asn—Gly—Gly—Phe—

35                  40                     45
Phe—Leu—Arg—Ile—His—Pro—Asp—Gly—Arg—Val—Asp—Gly—Val—Arg—Glu—

50                  55                     60
Lys—Ser—Asp—Pro—His—Ile—Lys—Leu—Gln—Leu—Gln—Ala—Glu—Glu—Arg—

65                  70                     75
Gly—Val—Val—Ser—Ile—Lys—Gly—Val—Cys—Ala—Asn—Arg—Tyr—Leu—Ala—

80                  85                     90
Met—Lys—Glu—Asp—Gly—Arg—Leu—Leu—Ala—Ser—Lys—Cys—Val—Thr—Asp—

95                 100                    105
Glu—Cys—Phe—Phe—Phe—Glu—Arg—Leu—Glu—Ser—Asn—Asn—Tyr—Asn—Thr—
```

```
            110                    115                    120
Tyr—Arg—Ser—Arg—Lys—Tyr—Ser—Ser—Trp—Tyr—Val—Ala—Leu—Lys—Arg—

125                    130                    135
Thr—Gly—Gln—Tyr—Lys—Leu—Gly—Pro—Lys—Thr—Gly—Pro—Gly—Gln—Lys—

140                145  146
Ala—Ile—Leu—Phe—Leu—Pro—Met—Ser—Ala—Lys—Ser.
```

The C-terminus of the native molecule is free acid.

The present invention provides two families of FGF antagonists which are each based upon a central fragment from the native hormone bFGF. The core of the first is those residues appearing at positions 36–39, and the core of the second appears to be those residues appearing at positions 106–115. In other words, relatively short peptides containing the four residues of the first family, as well as the tetrapeptide itself, show some suppression of endothelial cell growth, when growing under nonstimulated conditions (serum alone) and also when serum is supplemented by the addition of FGF to in vitro cell cultures. The FGF antagonism of the first family is found to be very substantially increased by the inclusion of N-terminal and/or C-terminal extensions to the tetrapeptide. These extensions may comprise the residue sequences normally found at these locations in the native hormone, e.g., bFGF(30–50) and are preferably, but not necessarily, amidated at the C-terminus. Preferably, the extended fragment includes bFGF(24–68) which exhibits good FGF antagonism. Some substitutions may be made in the sequence at selected locations, as discussed hereinafter.

The basis for the antagonistic action exhibited by these peptides is an interaction with the FGF receptor. Peptides that show antagonism to mitogenesis in vitro (including all FGF target cell types) also prevent FGF from binding to its receptor, and it appears the minimum length peptide should contain either the core sequence of bFGF (36–39) or bFGF (106–115).

In the peptidic fragments of the second family, which are generally within the sequence of bFGF (93–120) and which are also antagonistic, there is also a distinct heparin-binding site, i.e., a sequence contained within the peptide fragment binds radioactive heparin as well as the receptor. Because heparin is an important element in certain FGF action, peptides that inhibit binding between FGF and heparin may well also exhibit the important capacity to inhibit the biological action of FGF, which may be an inhibition of the binding of FGF to its receptor resulting from this interaction between FGF and heparin. However, it appears that it may be possible to design FGF antagonists that will bind strongly to the receptor and not bind strongly to heparin; for example, by replacing certain of the residues that account for binding to heparin, e.g., those in positions 107–110, analogs should result which will not bind heparin without substantially detracting from binding to the FGF receptor. The specificity of fragments related to bFGF(24–68) and bFGF(93–120) is best illustrated by a) their effects on all three parameters of FGF action (i.e., mitogenesis, heparin-binding and receptor interaction) and b) the observation that other FGF peptide fragments which do not contain either of the afore-mentioned core sequences fail to exhibit similar activity.

The first family of FGF antagonist peptides provided by the invention may be expressed by the following formula (which is based upon the naturally occurring sequence of bovine bFGF): Tyr-Cys-Lys-Asn-Gly-Gly-Phe-Phe-Leu-Arg-Ile-His-Pro-Asp-Gly-Arg-Val-Asp-$R_{42}$-Val-Arg-Glu-Lys-$R_{47}$-Asp-Pro-His-Ile-Lys-Leu-Gln-Leu-Gln-Ala-Glu-Glu-Arg-Gly-Val-Val-Ser-Ile-Lys-Gly-Val-Y wherein Y is either OH or $NH_2$. $R_{42}$ may be Gly or Ala or Sar, and $R_{47}$ may be Ser or Ala or Thr. Sar is the abbreviation for sarcosine. Peptides having this entire length, i.e., 45 residues, function as FGF antagonists and not as partial agonists. As such, they suppress endothelial cell growth both in the presence of basal FGF as well as in the presence of added FGF. 45 residues is not considered to be a maximum limit for a peptide that will function as an FGF antagonist, a main function of such an antagonist being simply to block the receptor on the endothelial cells without causing activation. As a result, additional residues may be added to either or both termini so long as the presence of these additional residues does not either (a) turn the peptide into a partial FGF agonist or (b) detract from the binding of the peptide to the receptor so as to lessen its biological activity as an FGF antagonist.

The second family of FGF antagonist peptides provided by the invention may be expressed by the following formula (which is based on the naturally occurring sequence of bovine bFGF): Phe-Phe-Phe-Glu-Arg-Leu-Glu-Ser-Asn-Asn-Tyr-Asn-Thr-Tyr-Arg-Ser-Arg-Lys-Tyr-$R_{112}$-$R_{113}$-$R_{114}$-$R_{115}$-Val-Ala-Leu-Lys-Arg-Y, wherein one or more of the residues in the sequence: Tyr-Arg-Ser-Arg-Lys-Tyr can be substituted by its D-isomer, $R_{112}$ is Ser, Thr or D-Ser, $R_{113}$ is Ser, Ala or D-Ser, $R_{114}$ is Trp or Met, $R_{115}$ is Tyr or Phe, and Y is either OH or $NH_2$. These peptides function as FGF antagonists, suppressing endothelial cell growth (and growth in other FGF target cells) in the presence or absence of FGF, and peptides shorter in length which include the core sequence bFGF(106–115) are also effective to act as antagonists to FGF. Although various of these peptides may also exhibit some agonist activity, if residues are be added to either or both termini of this 28-residue sequence, such changes may result in some receptor activation, creating competitive antagonists having still greater agonist activity.

It may be preferable to synthesize peptides which are about 45 amino acids or greater in length by using recombinant DNA methods. On the other hand, it may be preferable to synthesize peptides of about 30 residues or less in length using the well-known chain elongation techniques, such as solid-phase synthesis, as on a Merrifield resin or the like.

To synthesize a bFGF peptide containing only naturally occurring amino acid residues by recombinant DNA, a double-stranded DNA chain which encodes the desired amino acid sequence is synthetically constructed. The degeneracy of the genetic code permits a wide variety of codon combinations to be used to form the DNA chain that encodes the product polypeptide. Certain particular codons are more efficient for polypeptide expression in certain types of organisms, and the selection of codons preferably is made according to those codons which are most efficient for expression in the type of organism which is to serve as the host for the recombinant vector. However, any correct set of codons should encode the desired product, even if slightly less efficiently. Codon selection may also depend upon vector construction considerations; for example, it may be necessary to avoid creating a particular restriction site in the DNA chain if, subsequent to insertion of the synthetic DNA chain, the vector is to be manipulated using a restriction enzyme that cleaves at such a site. Also, it is necessary to avoid placing restriction sites in the DNA chain if the host organism which is to be transformed with the recombinant vector containing the DNA chain is known to produce a restriction enzyme that would cleave at such a site within the DNA chain.

In addition to the bFGF antagonist-encoding sequences, the DNA chain that is synthesized may contain additional sequences, depending upon vector construction considerations. Typically, a DNA chain is synthesized with linkers at its ends to facilitate insertion into restriction sites within a cloning vector. The DNA chain may be constructed so as to encode the desired sequence as a portion of a fusion polypeptide; and if so, it will generally contain terminal sequences that encode amino acid residue sequences that serve as proteolytic processing sites, whereby the desired polypeptide may be proteolytically cleaved from the remainder of the fusion polypeptide. The terminal portions of the synthetic DNA chain may also contain appropriate start and stop signals.

To assemble the desired DNA chain, oligonucleotides are constructed by conventional methods, such as procedures described in T. Maniatis et al., *Cold Spring Harbor Laboratory Manual.* Cold Spring Harbor, N.Y. (1982)(hereinafter, *CSH*). Sense and antisense oligonucleotide chains, up to about 70 nucleotide residues long, are synthesized, preferably on automated synthesizers, such as the Applied Biosystem Inc. model 380A DNA synthesizer. The oligonucleotide chains are constructed so that portions of the sense and antisense oligonucleotides overlap, associating with each other through hydrogen bonding between complementary base pairs and thereby forming double stranded chains, in most cases with gaps in the strands. Subsequently, the gaps in the strands are filled in and oligonucleotides of each strand are joined end to end with nucleotide triphosphates in the presence of appropriate DNA polymerases and/or with ligases.

As an alternative to construction of a synthetic DNA chain through oligonucleotide synthesis, when a peptide is desired that is a segment of the naturally occurring molecule, cDNA corresponding to the desired bFGF fragment may be prepared. A cDNA library or an expression library is produced in a conventional manner by reverse transcription from messenger RNA (mRNA) from a bFGF-producing cell line. To select clones containing bFGF sequences, hybridization probes (preferably mixed probes to accommodate the degeneracy of the genetic code) corresponding to portions of the bFGF protein are produced and used to identify clones containing such sequences. Screening of the expression library with bFGF antibodies may also be used, alone or in conjunction with hybridization probing, to identify or confirm the presence of bFGF-encoding DNA sequences in DNA library clones. Such techniques are taught, for example in *CSH*,supra.

The double-stranded bFGF-encoding DNA chain is shortened appropriately to the desired length to create the peptide of interest and then modified as necessary to permit its insertion into a particular appropriate cloning vector in mind. The cloning vector that is to be recombined to incorporate the DNA chain is selected appropriate to its viability and expression in a host organism or cell line, and the manner of insertion of the DNA chain depends upon factors particular to the host. For example, if the DNA chain is to be inserted into a vector for insertion into a prokaryotic cell, such as *E. Coli,* the DNA chain will be inserted 3' of a promoter sequence, a Shine-Delgarno sequence (or ribosome binding site) that is within a 5' non-translated portion and an ATG start codon. The ATG start codon is appropriately spaced from the Shine-Delgarno sequence, and the encoding sequence is placed in correct reading frame with the ATG start codon. The cloning vector also provides a 3' non-translated region and a translation termination site. For insertion into a eukaryotic cell, such as a yeast cell or a cell line obtained from a higher animal, the FGF fragment-encoding oligonucleotide sequence is appropriately spaced from a capping site and in correct reading frame with an ATG start signal. The cloning vector also provides a 3' non-translated region and a translation termination site.

Prokaryotic transformation vectors, such as pBR322, pMB9, Col E1, pCRI, RP4 and lambda-phage, are available for inserting a DNA chain of the length necessary to encode the FGF fragments of interest with substantial assurance of at least some expression of the encoded polypeptide. Typically, such vectors are constructed or modified to have a unique restriction site(s) appropriately positioned relative to a promoter, such as the lac promoter. The DNA chain may be inserted with appropriate linkers into such a restriction site, with substantial assurance of production of FGF in a prokaryotic cell line transformed with the recombinant vector. To assure the proper reading frame, linkers of various lengths may be provided at the ends of the FGF peptide-encoding sequence. Alternatively, cassettes, which include sequences, such as the 5' region of the lac Z gene (including the operator, promoter, transcription start site, Shine Delgarno sequence and translation initiation signal), the regulatory region from the tryptophane gene (trp operator, promoter, ribosome binding site and translation initiator), and a fusion gene containing these two promoters, called the trp-lac or commonly called the Tac promoter, are available into which a synthetic DNA chain may be conveniently inserted before the cassette is inserted into a cloning vector of choice.

Similarly, eukaryotic transformation vectors, such as the cloned bovine papilloma virus genome, the cloned genomes of the murine retroviruses, and eukaryotic cassettes, such as the pSV-2 gpt system (described by Mulligan and Berg, *Nature* 277, 108-114, 1979), the Okayama-Berg cloning system (*Mol. Cell Biol.* 2, 161-170, 1982) and the expression cloning vector recently described by Genetics Institute (*Science* 228, 810-815, 1985), are available which provide substantial assurance of at least some expression of the FGF peptide in the transformed eukaryotic cell line.

Another way to produce bFGF fragments of desired length is to produce the polypeptide initially as a segment of a gene-encoded fusion polypeptide. In such case, the DNA chain is constructed so that the expressed polypeptide has enzymatic processing sites flanking the bFGF fragment sequence. A bFGF-fragment-encoding DNA chain may be inserted, for example, into the beta-galactosidase gene for insertion into *E. Coli*, in which case, the expressed fusion polypeptide is subsequently cleaved with appropriate proteolytic enzymes to release the bFGF fragment from beta-galactosidase peptide sequences.

An advantage of inserting the bFGF-fragment-encoding sequence so that it is expressed as a cleavable segment of a fusion polypeptide, e.g., as the bFGF-fragment sequence fused within the beta-galactosidase peptide sequence, is that the endogenous polypeptide into which the bFGF fragment sequence is inserted is generally rendered non-functional, thereby facilitating selection for vectors encoding the fusion peptide.

The peptides can be synthesized by suitable chain elongation or coupling-type methods, such as by exclusively solid-phase techniques, by partial solid-phase techniques, by fragment condensation or by classical solution couplings. The techniques of exclusively solid-phase synthesis are set forth in the textbook "Solid-Phase Peptide Synthesis", Stewart & Young, Pierce Chemical Co., Rockford, Ill., 1984, and are exemplified by the disclosure of U.S. Pat. No. 4,105,603, issued Aug. 8, 1978. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to coupling-type syntheses is the protection of the labile side-chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

Such an intermediate for the first family may have the formula: $X^1$Tyr($X^2$)-Cys($X^4$)-Lys($X^7$) -Gly-Gly -Phe-Phe-Leu-Arg($X^6$)-Ile-His($X^9$)-Pro-Asp($X^3$) Gly-Arg($X^6$)-Val-Asp($X^3$)-$R_{42}$-Val-Arg($X^6$)-Glu($X^3$)-Lys($X^7$)-$R_{47}$($X^5$)-Asp($X^3$)-Pro-His($X^9$)-Ile -Lys($X^7$)-Leu-Gln($X^8$)-Leu-Gln($X^8$)-Ala-Glu($X^3$)- Glu($X^3$)-Arg($X^6$)-Gly-Val-Val-Ser($X^5$)-Ile-Lys($X^7$)-Gly-Val-$X^{10}$.

Such an intermediate for the second family may have the formula: $X^1$-Phe-Phe-Phe-Glu($X^3$)-Arg($X^6$)-Leu-Glu($X^3$)-Ser($X^5$)-Asn($X^8$)-Asn($X^8$)-Tyr($X^2$)-Asn -Thr($X^5$)-Tyr($X^2$)-Arg($X^6$)-Ser($X^5$)-Arg($X^6$)-Lys($X^7$)-Tyr($X^2$)-Ser($X^5$)-Ser($X^5$)-Trp-Tyr($X^2$)-Val-Ala-Leu-Lys($X^7$)-Arg($X^6$)-$X^{10}$.

In these formulae: $X^1$ is either hydrogen or an alpha-amino protecting group. The alpha-amino protecting groups contemplated by $X^1$ are those known to be useful in the art of step-wise synthesis of polypeptides. Among the classes of alpha-amino protecting groups covered by $X^1$ are (1) acyl-type protecting groups, such as formyl, trifluoroacetyl, phthalyl, toluenesulfonyl(-Tos), benzensulfonyl, nitrophenylsulfenyl, tritylsulfenyl, o-nitrophenoxyacetyl, chloroacetyl, acetyl, and γ-chlorobutyryl; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethyloxycarbonyl, isopropyloxycarbonyl, ethoxycarbonyl, allyloxycarbonyl; (4) cycloalkyl urethan-type protecting groups, such as cyclopentyloxycarbonyl, adamantyloxycarbonyl, and cyclohexyloxycarbonyl; (5) thiourethan-type protecting groups, such as phenylthiocarbonyl; (6) alkyl-type protecting groups, such as triphenylmethyl (trityl), benzyl;(7) trialkylsilane groups, such as trimethylsilane. The preferred alpha-amino protecting group is BOC.

$X^2$ is a protecting group for the phenolic hydroxyl group of Tyr selected from the group consisting of tetrahydropyranyl, tert-butyl, trityl, Bzl, CBZ, Br-CBZ and 2,6-dichlorobenzyl. The preferred protecting group is 2,6-dichlorobenzyl. $X^2$ can be hydrogen which means that there is no protecting group on the hydroxyl group.

$X^3$ is hydrogen or an ester-forming protecting group for the carboxyl group of Asp or Glu and is selected from the group consisting of Bzl, cyclohexyl, cycloheptal, 2,6-dichlorobenzyl, methyl and ethyl.

$X^4$ is a protecting group for Cys selected from the group consisting of p-methoxy-benzyl(MeOBzl), p-methylbenzyl, acetamidomethyl, trityl and Bzl. The most preferred protecting group is p-methoxybenzyl. $X^4$ can also be hydrogen, meaning that there is no protecting group on the sulfhydryl.

$X^5$ is a protecting group for the hydroxyl group of Thr and Ser and is selected from the group consisting of acetyl, benzoyl, tert-butyl, trityl, tetrahydropyranyl, Bzl, 2,6-dichlorobenzyl and CBZ. The preferred protecting group is Bzl. $X^5$ can be hydrogen, which means there is no protecting group on the hydroxyl group.

$X^6$ is a protecting group for the guanido group of Arg selected from the group consisting of nitro, Tos, CBZ, adamantyloxycarbonyl, and BOC, or is hydrogen.

$X^7$ is hydrogen or a protecting group for the side-chain amino substituent of Lys. Illustrative of suitable side-chain amino protecting groups are 2-chlorobenzyloxycarbonyl(2-Cl-Z), Tos, CBZ, t-amyloxycarbonyl and BOC.

The selection of a side-chain amino protecting group is not critical except that it must be one which is not removed during deprotection of the alpha-amino groups during the synthesis. Hence, the alpha-amino protecting group and the side-chain amino protecting group cannot be the same.

$X^8$ is a protecting group for the side-chain amido group of Gln and/or Asn and is preferably xanthyl (Xan). Optionally $X^8$ can be hydrogen.

$X^9$ is a protecting group for the imidazole nitrogen of His, such as Tos or dinitrophenyl, or may be hydrogen.

$X^{10}$ is selected from the class consisting of OH, OCH₃, esters, amides, hydrazides, —O—CH₂-resin support and —NH-resin support, with the groups other than OH and amides being broadly considered as protecting groups.

In the formula for the intermediate, at least one of $X^1$, $X^2$, $X^3$, $X^4$, $X^5$, $X^6$, $X^7$, $X^8$, $X^9$ and $X^{10}$ is a protecting group.

In selecting a particular side-chain protecting group to be used in the synthesis of the peptides, the following rules are followed: (a) the protecting group should be stable to the reagent and under the reaction conditions selected for removing the alpha-amino protecting group at each step of the synthesis, (b) the protecting group should retain its protecting properties and not be split off under coupling conditions, and (c) the side-chain protecting group should be removable, upon the completion of the synthesis containing the desired amino acid sequence, under reaction conditions that will not alter the peptide chain.

The peptides are preferably prepared using solid phase synthesis, such as that described by Merrifield, *J. Am. Chem. Soc.*, 85, p 2149 (1963), although other equivalent chemical syntheses known in the art can also be used as previously mentioned. Solid-phase synthesis is commenced from the C-terminal end of the peptide by coupling a protected alpha-amino acid to a suitable resin. Such a starting material can be prepared by attaching alpha-amino-protected Val by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London) 38, 1597-98 (1966). Chloromethylated resins are commercially available from Bio Rad Laboratories, Richmond, California and from Lab. Systems, Inc. The preparation of such a resin is described by Stewart et al., "Solid Phase Peptide Synthesis"(Freeman & Co., San Francisco 1969), Chapter 1, pp 1-6. BHA and MBHA resin supports are commercially available and are generally used only when the desired polypeptide being synthesized has an alpha-carboxamide at the C-terminal.

For example, a peptide of the first family can be prepared by coupling Val, protected by BOC, to a chloromethylated resin according to the procedure of Monahan and Gilon, *Biopolymer* 12, pp 2513-19, 1973 when, for example, it is desired to synthesize such a peptide with free carboxy terminus. Following the coupling of BOC-Val, the alpha-amino protecting group is removed, as by using trifluoroacetic acid(TFA) in methylene chloride, TFA alone or HCl in dioxane. The deprotection is carried out at a temperature between about 0° C. and room temperature. Other standard cleaving reagents and conditions for removal of specific alpha-amino protecting groups may be used as described in Schroder & Lubke, "The Peptides", 1 pp 72-75 (Academic Press 1965).

After removal of the alpha-amino protecting group of Val, the remaining alpha-amino- and side-chain-protected amino acids are coupled stepwise in the desired order to obtain an intermediate compound as defined hereinbefore. As an alternative to adding each amino acid separately in the synthesis, some of them may be coupled to one another prior to their addition to the solid phase reactor. The selection of an appropriate coupling reagent is within the skill of the art; particularly suitable as a coupling reagent is N,N'-dicyclohexyl carbodiimide (DCCI).

Activating reagents used in solid phase synthesis of the peptides are well known in the peptide synthesis art. Examples of suitable activating reagents are: (1) carbodiimides, such as N,N'-diisopropyl carbodiimide, N-N'-dicyclohexylcarbodiimide(DCCI); (2) cyanamides such as N,N'-dibenzylcyanamide; (3) keteimines; (4) isoxazolium salts, such as N-ethyl-5-phenyl isoxazolium-3,-sulfonate; (5) monocyclic nitrogen-containing heterocyclic amides of aromatic character containing one through four nitrogens in the ring, such as imidazolides, pyrazolides, and 1,2,4-triazolides. Specific heterocyclic amides that are useful include N,N'-carbonyl diimidazole, N,N'-carbonyl-di-1,2,4-triazole; (6) alkoxylated acetylene, such as ethoxyacetylene; (7) reagents which form a mixed anhydride with the carboxyl moiety of the amino acid, such as ethylchloroformate and isobutylchloroformate and (8) reagents which form an active ester with the carboxyl moiety of the amino acid, such as nitrogen-containing heterocyclic compounds having a hydroxy group on one ring nitrogen, e.g. N-hydroxyphthalimide, N-hydroxysuccinimide and 1-hydroxybenzotriazole(HOBT). Other activating reagents and their use in peptide coupling are described by Schroder & Lubke supra, in Chapter III and by Kapoor, *J. Phar. Sci.*, 59, pp 1-27 (1970).

Each protected amino acid or amino acid sequence is introduced into the solid phase reactor in about a two-fold or more excess, and the coupling may be carried out in a medium of dimethylforaamide(DMF):$CH_2Cl_2$ (1:1) or in DMF or $CH_2Cl_2$ alone. In cases where incomplete coupling occurs, the coupling procedure is repeated before removal of the alpha-amino protecting group prior to the coupling of the next amino acid. If performed manually, the success of the coupling reaction at each stage of the synthesis is monitored by the ninhydrin reaction, as described by E. Kaiser et al., *Anal. Biochem.* 34, 595 (1970).

After the desired amino acid sequence has been completed, the intermediate peptide is removed from the resin support by treatment with a reagent, such as liquid hydrogen fluoride, which not only cleaves the peptide from the resin but also cleaves all remaining side-chain protecting groups $X^2$, $X^3$, $X^4$, $X^5$, $X^6$, $X^7$, $X^8$ and $X^9$ and the alpha-amino protecting group $X^1$ to obtain the peptide.

As an alternative route, the intermediate peptide may be separated from the resin support by alcoholysis after which the recovered C-terminal alkyl ester is converted to the acid by hydrolysis. Any side-chain protecting groups may then be cleaved as previously described or by other known procedures, such as catalytic reduction (e.g. Pd on $BaSO_4$) When using hydrogen fluoride for cleaving, anisole and methylethyl sulfide are included in the reaction vessel for scavenging.

The following examples set forth preferred methods for synthesizing FGF antagonists by the solid-phase technique. It will of course be appreciated that the synthesis of a correspondingly shorter peptide fragment is effected in the same manner by merely eliminating the requisite number of amino acids at either end of the chain.

EXAMPLE I

The synthesis of bFGF(24-68)-amide having the formula: H-Tyr-Cys-Lys-Asn-Gly-Gly-Phe-Phe-Leu-Arg-Ile-His-Pro-Asp-Gly-Arg-Val-Asp-Gly-Val-Arg-Glu-Lys-Ser-Asp-Pro-His-Ile-Lys-Leu-Gln-Leu-Gln-Ala-Glu-Glu-Arg-Gly-Val-Val-Ser-Ile-Lys-Gly-Val-$NH_2$ is conducted in a stepwise manner using a Beckman 990 Peptide Synthesizer and an MBHA resin. Coupling of BOC-Val to the resin is performed by the general procedure set forth in U.S. Pat. No. 4,292,313, and it results in the substitution of about 0.2–0.6 mmol Val per gram of resin depending on the substitution of the MHBA resin used.

After deprotection and neutralization, the peptide chain is built step-by-step on the resin. Deprotection, neutralization and addition of each amino acid is performed in general accordance with the procedure set forth in detail in Guillemin et al. U.S. Pat. No.

3,904,594. The couplings are specifically carried out as set out in the following schedule.

SCHEDULE

| STEP | REAGENTS AND OPERATIONS | MIX TIMES MIN. |
|---|---|---|
| 1 | CH$_2$Cl$_2$ wash (2 times) | 0.5 |
| 2 | 45% trifluoroacetic acid (TFA) + 5% 1,2-ethanedithiol in CH$_2$Cl$_2$ (1 time) | 0.5 |
| 3 | 45% trifluoroacetic acid (TFA) + 5% 1,2-ethanedithiol in CH$_2$Cl$_2$ (1 time) | 20.0 |
| 4 | CH$_2$Cl$_2$ wash (3 times) | 0.5 |
| 5 | CH$_3$OH wash (2 times) | 0.5 |
| 6 | 10% triethylamine (Et$_3$N) in CH$_2$Cl$_2$ neutralization (2 times) | 0.5 |
| 7 | CH$_3$OH wash (2 times) | 0.5 |
| 8 | 10% triethylamine (Et$_3$N) in CH$_2$Cl$_2$ neutralization (2 times) | 0.5 |
| 9 | CH$_3$OH wash (2 times) | 0.5 |
| 10 | CH$_2$Cl$_2$ wash (2 times) | 0.5 |
| 11 | *Boc-amino acid (1 mmole/g resin) plus equivalent amount of dicyclohexylcarbodiimide (DCC) in CH$_2$Cl$_2$ | 120 |
| 12 | CH$_2$Cl$_2$ wash (1 time) | 0.5 |
| 13 | 50% dimethylformamide in CH$_2$Cl$_2$ wash (2 times) | 0.5 |
| 14 | 10% triethylamine (Et$_3$N) in CH$_2$Cl$_2$ wash (1 time) | 0.5 |
| 15 | CH$_3$OH wash (2 times) | 0.5 |
| 16 | CH$_2$Cl$_2$ wash (2 times) | 0.5 |
| 17 | 25% acetic anhydride in CH$_2$Cl$_2$ (2 ml/g resin) | 20.0 |
| 18 | CH$_2$Cl$_2$ wash (2 times) | 0.5 |
| 19 | CH$_3$OH wash (2 times) | 0.5 |

*For the coupling of Asn and Gln, an 1.136 molar excess of 1-hydroxybenzotriazole (HOBt) is included in this step.

Briefly, for the coupling reaction, one mmol. of BOC-protected amino acid in methylene chloride is used per gram of resin, plus one equivalent of 0.5 molar DCCI in methylene chloride or 30% DMF in methylene chloride, for two hours. When Arg is being coupled, a mixture of 10% DMF and methylene chloride is used. Bzl is used as the hydroxyl side-chain protecting group for Ser and Thr. 2-chloro-benzyloxycarbonyl (2Cl-Z) is used as the protecting group for the Lys side chain. Tos is used to protect the guanidino group of Arg, and the Glu or Asp carboxyl group is protected as the Bzl ester. The phenolic hydroxyl group of Tyr is protected with 2,6-dichlorobenzyl. Asn and Gln are left unprotected. At the end of the synthesis, the following composition is obtained (X$^1$)Tyr(X$^2$)-Cys(X$^4$)-Lys(X$^7$)-Asn-Gly-Gly-Phe-Phe-Leu-Arg(X$^6$)-Ile-His(X$^9$)-Pro-Asp(X$^3$)gly-Arg(X$^6$-Val-Asp(X$^3$)-Gly-Val-Arg(X$^6$)-Glu(X$^3$)-Lys(X$^7$)-Ser(X$^5$)-Asp(X$^3$)-Pro-His(X$^9$)-Ile-Lys(X$^7$)-Leu-Gln-Leu-Gln-Ala-Glu(X$^3$)-Glu(X$^3$)-Arg(X$^6$)-Gly-Val-Val-Ser(X$^5$)-Ile-Lys(X$^7$)-Gly-Val-X$^{10}$ wherein X$^1$ is BOC, X$^2$ is 2,6-dichlorobenzyl, X$^3$ is benzyl ester, X$^4$ is MeOBzl, X$^5$ is Bzl, X$^6$ is Tos X$^7$ is 2Cl-Z, X$^9$ is Tos and X$^{10}$ is -NH-MBHA resin support.

After the final Tyr residue has been coupled to the resin, the BOC group is removed with 45% TFA in CH$_2$Cl$_2$ In order to cleave and deprotect the remaining protected peptide-resin, it is treated with 1.5 ml. anisole, 0.25 ml. methylethylsulfide and 10 ml. hydrogen fluoride (HF) per gram of peptide-resin, at −20° C. for one-half hour and at 0° C. for one-half hour. After elimination of the HF under high vacuum, the resin-peptide remainder is washed alternately with dry diethyl ether and chloroform, and the peptide is then extracted with degassed 2N aqueous acetic acid. Lyophilization of the acetic acid extract provides a white fluffy material.

The cleaved and deprotected peptide is then dissolved in 30% acetic acid and subjected to Sephadex G-50 fine gel filtration.

The peptide is then further purified by CM-32 carboxymethyl cellulose (Whatman) cation-exchange chromatography(1.8×18 cm., V$_{bed}$=50 ml.) using a concave gradient generated by dropping 1 L. of 0.4 M NH$_4$OAc, pH 6.5 into a mixing flask containing 400 ml. 0.01 M. NH$_4$OAc, pH 4.5. Final purification is carried out using preparative HPLC on a Vydec C$_4$ column using a 0.1% TFA and acetonitrile solvent system. Purification details are generally set forth in Ling et al. *Biochem. Biophys. Res. Commun.* 95, 945 (1980). The chromatographic fractions are carefully monitored by TLC, and only the fractions showing substantial purity are pooled.

The synthesis is repeated using a chloromethylated resin to produce the same peptide having a free acid C-terminus, generally following the procedure described in *Biopolymers*, 12, 2513-19 (1973) to link Val to the chloromethylated resin.

EXAMPLE II

To determine the effectiveness of the bFGF fragment peptide to inhibit the growth of endothelial cells, the peptide is tested under conditions to measure its ability to modulate both basal cell growth and bFGF-simulated cell proliferation. A bioassay was employed of the type set forth in detail in Gospodarowicz et al., *J. Cell Biol.*, 122, 323-333 (1985), using BAAE cells.

For each test, an initial cell density of between about 0.3–0.5×10$^4$ cells per well was established in 24-miniwell plates. After 6-8 hours, the cells in each well were treated with a challenge dose of bFGF in the absence, or presence to a varying concentration, of a synthetic FGF antagonist. The precise treatment was repeated 48 hours later. On the fifth day, the cells were digested with trypsin, and the total number of cells in each well was determined using a Coulter particle counter. Testing of the peptide bFGF(24–68)-NH$_2$ shows full antagonist activity to both basal cell growth and to bFGF-stimulated cell growth, with cell population being reduced by about 84% and about 92%, respectively, at a concentration of about 100 μg/ml. Like results are obtained from the testing of bFGF(24–68)-OH, with both peptides exhibiting an ID$_{50}$ of about 5 micromoles.

Testing is then carried out to determine the effect of the fragments of bFGF on the binding of I$^{125}$-bFGF to BHK cells, in order to determine the interaction with the receptors of FGF target cells, and is also carried out to determine the binding of the fragments to [$^3$H]-heparin. bFGF(24–68)-NH$_2$, at a concentration of 100 μg/ml., reduces the amount of radioactive bFGF bound to the cells by about 54% and shows strong affinity to bind heparin.

EXAMPLE III

The synthesis of -bFGF(30–50)-NH$_2$ having the formula: H-Phe-Phe-Leu-Arg-Ile-His-Pro-Asp-Gly-Arg-Val-Asp-Gly-Val-Arg-Glu-Lys-Ser-Asp-Pro-Tyr-NH$_2$ is conducted in a stepwise manner using a Beckman 990 synthesizer and an MBHA resin in the manner described in Example I. The peptide is judged to be substantially pure using TLC and HPLC. Testing in the manner set forth in Example II shows that the peptide has full antagonist activity to both basal and bFGF-stimulated endothelial cell growth, reducing cell population by about 19% and about 16%, respectively.

EXAMPLE IV

The synthesis of bFGF(30-49)-NH$_2$ having the formula: H-Phe-Phe-Leu-Arg-Ile-His-Pro-Asp-Gly-Arg-Val- Asp-Gly-Val-Arg-Glu-Lys-Ser-Asp-Pro-NH$_2$ is conducted in a stepwise manner using a Beckman 990 synthesizer and an MBHA resin in the manner described in Example I except that cyclohexyl instead of Bzl is used to protect Asp and Glu. The peptide is judged to be substantially pure using TLC and HPLC. Testing in the manner set forth in Example II shows that the peptide has full antagonist activity to both basal and FGF-stimulated endothelial cell growth.

EXAMPLE IV A

The synthesis of bFGF(25-37)-NH$_2$ having the formula: H-Cys-Lys-Asn-Gly-Gly-Phe-Phe-Leu-Arg-Ile-His-Pro-Asp-NH$_2$ is conducted in a stepwise manner using a Beckman 990 synthesizer and an MBHA resin in the manner described in Example I. The peptide is judged to be substantially pure using TLC and HPLC. Testing in the manner set forth in Example II shows that the peptide has some antagonist activity to basal endothelial cell growth and has a fairly strong binding affinity for heparin and a fair affinity for BHK cells.

EXAMPLE V

The synthesis of [Tyr$^{25}$]-bFGF(25-68)-NH$_2$ having the formula: H-Tyr-Lys-Asn-Gly-Gly-Phe-Phe-Leu-Arg-Ile-His-Pro-Asp-Gly-Arg-Val-Asp-Gly-Val-Arg-Glu-Lys-Ser-Asp-Pro-His-Ile-Lys-Leu-Gln-Leu-Gln-Ala-Glu-Glu-Arg-Gly-Val-Val-Ser-Ile-Lys-Gly-Val-NH$_2$ is conducted in a stepwise manner using a Beckman 990 synthesizer and an MBHA resin in the manner described in Example I. The peptide is judged to be substantially pure using TLC and HPLC. Testing in the manner set forth in Example II shows that the peptide has full antagonist activity to both basal and bFGF-stimulated endothelial cell growth, reducing cell population by about 86% and about 95%, respectively, and that it has a very strong binding affinity for BHK cells and heparin.

EXAMPLE VI

The synthesis of [Tyr$^{30,50}$]-bFGF(30-50)-OH having the formula: H-Tyr-Phe-Leu-Arg-Ile-His-Pro-Asp-Gly-Arg-Val-Asp-Gly-Val-Arg-Glu-Lys-Ser-Asp-Pro-Tyr-OH is conducted in a stepwise manner using a Beckman 990 synthesizer and a chloromethylated resin in the manner described hereinbefore. The peptide is judged to be substantially pure using TLC and HPLC. Testing in the manner set forth in Example II shows that the peptide has full antagonist activity to both basal and bFGF-stimulated endothelial cell growth.

EXAMPLE VII

The synthesis of bFGF(32-53)-NH$_2$ having the formula: H-Leu-Arg-Ile-His-Pro-Asp-Gly-Arg-Val-Asp-Gly-Val-Arg-Glu-Lys-Ser-Asp-Pro-His-Ile-Lys-Leu-NH$_2$ is conducted in a stepwise manner using a Beckman 990 synthesizer and an MBHA resin in the manner described in Example I. The peptide is judged to be substantially pure using TLC and HPLC. Testing in the manner set forth in Example II shows that the peptide has weak antagonist activity to both basal and bFGF-stimulated endothelial cell growth.

EXAMPLE VIII

The synthesis of bFGF(32-39)-N$_2$ having the formula H-Leu-Arg-Ile-His-Pro-Asp-Gly-Arg-NH$_2$ is conducted in a stepwise manner using a Beckman 990 synthesizer and an MBHA resin in the manner described in Example I. The peptide is judged to be substantially pure using TLC and HPLC. Testing in the manner set forth in Example II shows that the peptide has full antagonist activity to both basal and bFGF-stimulated endothelial cell growth, reducing cell population by about 37% and about 11%, respectively.

EXAMPLE IX

The synthesis of bFGF(24-63)-NH$_2$ having the formula: H-Tyr-Cys-Lys-Asn-Gly-Gly-Phe-Phe-Leu-Arg-Ile-His-Pro-Asp-Gly-Arg-Val-Asp-Gly-Val-Arg-Glu-Lys-Ser-Asp-Pro-His-Ile-Lys-Leu-Gln-Leu-Gln-Ala-Glu-Glu-Arg-Gly-Val-Val-NH$_2$ is conducted in a stepwise manner using a Beckman 990 synthesizer and a MBHA resin in the manner described in Example I. The peptide is judged to be substantially pure using TLC and HPLC. Testing in the manner set forth in Example II shows that the peptide has full antagonist activity to both basal and bFGF-stimulated endothelial cell growth.

EXAMPLE X

The synthesis of [Ala$^{47}$]-bFGF(24-63)-NH$_2$ having the formula: H-Tyr-Cys-Lys-Asn-Gly-Gly-Phe-Phe-Leu-Arg-Ile-His-Pro-Asp-Gly-Arg-Val-Asp-Gly-Val-Arg-Glu-Lys-Ala-Asp-Pro-His-Ile-Lys-Leu-Gln-Leu-Gln- Ala-Glu-Glu-Arg-Gly-Val-Val-NH$_2$ is conducted in a stepwise manner using a Beckman 990 synthesizer and an MBHA resin in the manner described in Example I. The peptide is judged to be substantially pure using TLC and HPLC. Testing in the manner set forth in Example II shows that the peptide has full antagonist activity to both basal and bFGF-stimulated endothelial cell growth.

EXAMPLE XI

The synthesis of [Sar$^{42}$]-bFGF(36-68)-NH$_2$ having the formula: H-Pro-Asp-Gly-Arg-Val-Asp-Sar-Val-Arg-Glu-Lys-Ser-Asp-Pro-His-Ile-Lys-Leu-Gln-Leu-Gln-Ala-Glu-Glu-Arg-Gly-Val-Val-Ser-Ile-Lys-Gly-Val-NH$_2$ is conducted in a stepwise manner using a Beckman 990 synthesizer and an MBHA resin in the manner described in Example I. The peptide is judged to be substantially pure using TLC and HPLC. Testing in the manner set forth in Example II shows that the peptide has full antagonist activity to both basal and bFGF-stimulated endothelial cell growth.

EXAMPLE XII

The synthesis of [Ala$^{42}$]-bFGF(36-68)-NH$_2$ having the formula: H-Pro-Asp-Gly-Arg-Val-Asp-Ala-Val-Arg-Glu-Lys-Ser-Asp-Pro-His-Ile-Lys-Leu-Gln-Leu-Gln-Ala-Glu-Glu-Arg-Gly-Val-Val-Ser-Ile-Lys-Gly-Val-NH$_2$ is conducted in a stepwise manner using a Beckman 990 synthesizer and an MBHA resin in the manner described in Example I. The peptide is judged to be substantially pure using TLC and HPLC. Testing in the manner set forth in Example II shows that the peptide has full antagonist activity to both basal and bFGF-stimulated endothelial cell growth.

EXAMPLE XIII

The synthesis of bFGF(35–50)-NH$_2$ having the formula: H-His-Pro-Asp-Gly-Arg-Val-Asp-Gly-Val-Arg-Glu-Lys-Ser-Asp-Pro-His-NH$_2$ is conducted in a stepwise manner using a Beckman 990 synthesizer and an MBHA resin in the manner described in Example I. The peptide is judged to be substantially pure using TLC and HPLC. Testing in the manner set forth in Example II shows that the peptide has full antagonist activity to both basal and bFGF-stimulated endothelial cell growth.

EXAMPLE XIV

The synthesis of [Ala$^{42}$, Thr$^{47}$]-bFGF(35–50-NH$_2$ having the formula: H-His-Pro-Asp-Gly-Arg-Val-Asp-Ala-Val-Arg-Glu-Lys-Thr-Asp-Pro-His-NH$_2$ is conducted in a stepwise manner using a Beckman 990 synthesizer and an MBHA resin in the manner described in Example I. The peptide is judged to be substantially pure using TLC and HPLC. Testing in the manner set forth in Example II shows that the peptide has full antagonist activity to both basal and bFGF-stimulated endothelial cell growth.

EXAMPLE XV

The synthesis of bFGF(36–39)-NH$_2$ having the formula: H-Pro-Asp-Gly-Arg-NH$_2$ is conducted in a stepwise manner using a Beckman 990 synthesizer and an MBHA resin in the manner described in Example I. The tetrapeptide is judged to be substantially pure using TLC and HPLC. Testing in the manner set forth in Example II shows that the peptide has full antagonist activity to both basal and bFGF-stimulated endothelial cell growth, reducing cell population by about 37% and about 54%, respectively. It has biological potency less than that of bFGF(24–68), exhibiting an ID$_{50}$ at between about 30 and 50 micromoles.

EXAMPLE XVI

The synthesis of bFGF(93–120)-NH$_2$ having the formula: H-Phe-Phe-Phe-Glu-Arg-Leu-Glu-Ser-Asn-Asn-Tyr-Asn-Thr-Tyr-Arg-Ser-Arg-Lys-Tyr-Ser-Ser-Trp-Tyr-Val-Ala-Leu-Lys-Arg-NH$_2$ is conducted in a stepwise manner using a Beckman 990 synthesizer and an MBHA resin in the manner described in Example I. The peptide is judged to be substantially pure using TLC and HPLC. Testing in the manner set forth in Example II shows that the peptide has full antagonist activity to both basal and bFGF-stimulated endothelial cell growth, that it binds to heparin, and that it inhibits the binding of bFGF to BHK cells.

EXAMPLE XVII

The synthesis of bFGF(106–118)-NH$_2$ having the formula: H-Tyr-Arg-Ser-Arg-Lys-Tyr-Ser-Ser-Trp-Tyr-Val-Ala-Leu-NH$_2$ is conducted in a stepwise manner using a Beckman 990 synthesizer and an MBHA resin in the manner described in Example I. The peptide is judged to be substantially pure using TLC and HPLC. Testing in the manner set forth in Example II shows that the peptide has partial antagonist activity in mitogenic assays and inhibits binding of bFGF to its receptor in BHK cells.

EXAMPLE XVIII

The synthesis of bFGF(103–146)-NH$_2$ having the formula: H-Tyr-Asn-Thr-Tyr-Arg-Ser-Arg-Lys-Tyr-Ser-Ser-Trp-Tyr-Val-Ala-Leu-Lys-Arg-Thr-Gly-Gln-Tyr-Lys-Leu-Gly-Pro-Lys-Thr-Gly-Pro-Gly-Gln-Lys-Ala-Ile-Leu-Phe-Leu-Pro-Met-Ser-Ala-Lys-Ser-NH$_2$ is conducted in a stepwise manner using a Beckman 990 synthesizer and an MBHA resin in the manner described in Example I. The peptide is judged to be substantially pure using TLC and HPLC. Testing in the manner set forth in Example II shows that the peptide very strongly inhibits FGF binding to BHK cells and to heparin.

EXAMPLE XVIII A

The synthesis of bFGF(97–120)-NH$_2$ having the formula: H-Arg-Leu-Glu-Ser-Asn-Asn-Tyr-Asn-Thr-Tyr-Arg-Ser-Arg-Lys-Tyr-Ser-Ser-Trp-Tyr-Val-Ala-Leu-Lys-Arg-NH$_2$ is conducted in a stepwise manner using a Beckman 990 synthesizer and an MBHA resin in the manner described in Example I. The peptide is judged to be substantially pure using TLC and HPLC. Testing is carried out using a culture of serum-starved 3T3 cells which are incubated for 24 hours with the bFGF peptide fragment and a challenge dose of bFGF and then incubated for 5 hours with radioactive [$^3$H]-thymidine to determine whether the fragment will inhibit the incorporation of [$^3$H]-DNA in the cell line which will be indicative of its inhibiting cell growth. It is shown that the peptide exhibits very good inhibition of bFGF-induced mitosis, and further testing shows that it very strongly inhibits bFGF binding to BHK cells and that it binds itself to heparin.

EXAMPLE XVIII B

The synthesis of bFGF(100–120)-NH$_2$ having the formula: H-Ser-Asn-Asn-Tyr-Asn-Thr-Tyr-Arg-Ser-Arg-Lys-Tyr-Ser-Ser-Trp-Tyr-Val-Ala-Leu-Lys-Arg-NH$_2$ is conducted in a stepwise manner using a Beckman 990 synthesizer and an MBHA resin in the manner described in Example I. The peptide is judged to be substantially pure using TLC and HPLC. Testing is carried out using a culture of serum-starved 3T3 cells which are incubated for 24 hours with the bFGF peptide fragment and a challenge dose of bFGF and then incubated for 5 hours with radioactive [$^3$H]-thymidine to determine whether the fragment will inhibit the incorporation of [$^3$H]-DNA in the cell line which will be indicative of its inhibiting cell growth. It is shown that the peptide exhibits very good inhibition of bFGF-induced mitosis, and further testing shows that it very strongly inhibits bFGF binding to BHK cells and that it binds itself to heparin.

EXAMPLE XVIII C

The synthesis of bFGF(103–120)-NH$_2$ having the formula: H-Tyr-Asn-Thr-Tyr-Arg-Ser-Arg-Lys-Tyr-Ser-Ser-Trp-Tyr-Val-Ala-Leu-Lys-Arg-NH$_2$ is conducted in a stepwise manner using a Beckman 990 synthesizer and an MBHA resin in the manner described in Example I. The peptide is judged to be substantially pure using TLC and HPLC. Testing is carried out using a culture of serum-starved 3T3 cells which are incubated for 24 hours with the bFGF peptide fragment and a challenge dose of bFGF and then incubated for 5 hours with radioactive [$^3$H]-thymidine to determine whether the fragment will inhibit the incorporation of [$^3$H]-DNA in the cell line which will be indicative of its inhibiting cell growth. It is shown that the peptide exhibits very good inhibition of bFGF-induced cell mitosis; further testing shows that it very strongly inhibits binding of bFGF to BHK cells and that it binds to heparin.

EXAMPLE XVIII D

The synthesis of bFGF(106–120)-NH$_2$ having the formula: H-Tyr-Arg-Ser-Arg-Lys-Tyr-Ser-Ser-Trp-Tyr-Val-Ala-Leu-Lys-Arg-NH$_2$ is conducted in a stepwise manner using a Beckman 990 synthesizer and an MBHA resin in the manner described in Example I. The peptide is judged to be substantially pure using TLC and HPLC. Testing is carried out using a culture of serum-starved 3T3 cells which are incubated for 24 hours with the bFGF peptide fragment and a challenge dose of bFGF and then incubated for 5 hours with radioactive [$^3$H]-thymidine to determine whether the fragment will inhibit the incorporation of [$^3$H]-DNA in the cell line which will be indicative of its inhibiting cell growth. It is shown that the peptide exhibits very good inhibition of bFGF-induced cell mitosis; further testing shows that it very strongly inhibits binding of bFGF to BHK cells and that it binds to heparin.

EXAMPLE XVIII E

The synthesis of [Met$^{114}$]-bFGF(106–120)-NH$_2$ having the formula: H-Tyr-Arg-Ser-Arg-Lys-Tyr-Ser-Ser-Met-Tyr-Val-Ala-Leu-Lys-Arg-NH$_2$ is conducted in a stepwise manner using a Beckman 990 synthesizer and an MBHA resin in the manner described in Example I. The peptide is judged to be substantially pure using TLC and HPLC. Testing is carried out as described in Example XVIIID. The peptide exhibits very good inhibition of bFGF-induced cell mitosis and very strongly inhibits binding of bFGF to BHK cells.

EXAMPLE XVIII F

The synthesis of [Phe$^{115}$]-bFGF(106–120)-NH$_2$ having the formula: H-Tyr-Arg-Ser-Arg-Lys-Tyr-Ser-Ser-Trp-Phe-Val-Ala-Leu-Lys-Arg-NH$_2$ is conducted in a stepwise manner using a Beckman 990 synthesizer and an MBHA resin in the manner described in Example I. The peptide is judged to be substantially pure using TLC and HPLC. Testing is carried out as described in Example XVIIID. The peptide exhibits very good inhibition of bFGF-induced cell mitosis and very strongly inhibits binding of bFGF to BHK cells.

EXAMPLE XVIII G

The synthesis of bFGF(106–115)-NH$_2$ having the formula: H-Tyr-Arg-Ser-Arg-Lys-Tyr-Ser-Ser-Trp-Tyr-NH$_2$ is conducted in a stepwise manner using a Beckman 990 synthesizer and an MBHA resin in the manner described in Example I. The peptide is judged to be substantially pure using TLC and HPLC. Testing is carried out using a culture of serum-starved 3T3 cells which are incubated for 24 hours with the bFGF peptide fragment and a challenge dose of bFGF and then incubated for 5 hours with radioactive [$^3$H]-thymidine to determine whether the fragment will inhibit the incorporation of [$^3$H]-DNA in the cell line which will be indicative of its inhibiting cell growth. It is shown that the peptide exhibits very good inhibition of bFGF-induced cell mitosis; further testing shows that it very strongly inhibits binding of bFGF to BHK cells and that it binds to heparin.

EXAMPLE XVIII H

The syntheses of the following compounds are conducted in a stepwise manner using a Beckman 990 synthesizer and an MBHA resin in the manner described in Example I:

bFGF(106–125)-NH$_2$,
bFGF(106–130)-NH$_2$,
bFGF(106–135)-NH$_2$,
bFGF(106–140)-NH$_2$,
bFGF(106–146)-NH$_2$.

These peptides are each judged to be substantially pure using TLC and HPLC. Testing in the manner set forth in Example II shows that all the peptides exhibit strong inhibition of bFGF binding to the receptor and inhibition of bFGF induced mitosis.

EXAMPLE XVIII J

The syntheses of the following compounds are conducted in a stepwise manner using a Beckman 990 synthesizer and an MBHA resin in the manner described in Example I:

[D-Tyr$^{106}$]-bFGF(106–120)-NH$_2$,
[D-Arg$^{107}$]-bFGF(106–120)-NH$_2$,
[D-Ser$^{108}$]-bFGF(106–120)-NH$_2$,
[D-Arg$^{109}$]-bFGF(106–120)-NH$_2$,
[D-Lys$^{110}$]-bFGF(106–120)-NH$_2$,
[D-Tyr$^{111}$]-bFGF(106–120)-NH$_2$,
[D-Ser$^{112}$]-bFGF(106–120)-NH$_2$, and
[D-Ser$^{113}$]-bFGF(106–120)-NH$_2$.

These peptides are each judged to be substantially pure using TLC and HPLC. Testing in the manner set forth in Example II shows inhibition of bFGF binding to the FGF receptors of BHK cells nearly as strong as does bFGF(106–120)-NH$_2$. Moreover, D-Ser$^{113}$ showed inhibition to bFGF-induced mitosis substantially as strong as bFGF(106–120)-NH$_2$.

EXAMPLE XVIII K

The synthesis of [Ala$^{113}$]-bFGF(103–146)-NH$_2$ having the formula: H-Tyr-Asn-Thr-Tyr-Arg-Ser-Arg-Lys-Tyr-Ser-Ala-Trp-Tyr-Val-Ala-Leu-Lys-Arg-Thr-Gly-Gln-Tyr-Lys-Leu-Gly-Pro-Lys-Thr-Gly-Pro-Gly-Gln-Lys-Ala-Ile-Leu-Phe-Leu-Pro-Met-Ser-Ala-Lys-Ser-NH$_2$ is conducted in a stepwise manner using a Beckman 990 synthesizer and an MBHA resin in the manner described in Example I. The peptide is judged to be substantially pure using TLC and HPLC. Testing in the manner set forth in Example II shows that the peptide very strongly inhibits FGF binding to BHK cells.

EXAMPLE XIX

Using conventional methods, described in *CSH. supra.*, a synthetic bFGF-fragment gene is constructed having the following formula:

```
5' AATTCATGTATTGTAAAAACGGGGGGTTC
3'     GTACATAACATTTTTGCCCCCCAAG

TTCCTACGAATCCACCCAGATGGGCGAGTAGATGGGGTACGAGAA
AAGGATGCTTAGGTGGGTCTACCCGCTCATCTACCCCATGCTCTT
```

```
AAATCCGATCCACACATCAAACTACAACTACAAGCCGAAGAACGA
TTTAGGCTAGGTGTGTAGTTTGATGTTGATGTTCGGCTTCTTGCT

GGGGTAGTATCCATCAAAGGGGTATAAG      3'
CCCCATCATAGGTAGTTTCCCCATATTCAGCT 5'
```

Synthesis of such a bFGF-fragment-encoding DNA chain is accomplished by synthesizing oligonucleotides on an Applied Biosystems automatic synthesizer with overlapping complementary sequences.

The overlapping oligonucleotides are fused to form a double-stranded DNA chain, gaps being filled in with DNA polymerase and with T4 ligase. Immediately 5, of the bFGF-fragment-encoding sequence in the sense strand is provided an ATG start signal, which results in an extraneous methionine being added to the N-terminus of the expressed polypeptide. Immediately 3' of the bFGF-fragment-encoding sequence is a stop signal. At the 5' end is a Eco RI overhang and at the 4' end is a Sal I overhang, whereby the synthetic DNA strand is directly insertable in the Eco RI and Sal I site of the plasmid pUC8, described by Vieira et al. *Gene* 14, 259-268 (1982). The DNA strand is annealed into the pUC$_8$ plasmid where it is under the control of the beta galactosidase promoter with the ATG start signal and the Shine Delgarno sequence retained in their natural orientation and association with the promoter.

The recombinant vector, designated bFGF(24-68), is transformed into the DH-1 strain of *E. Coli* by the calcium chloride procedure, *CSH*, supra.

The transformed *E. Coli* is cultured in L broth, and ampicillin-resistant strains are selected. Because the DNA chain was inserted into the plasmid in an orientation which could be expected to lead to expression of protein product of the DNA chain, the ampicillan-resistant colonies are screened for reactivity with antiserum raised against bFGF. These colonies are screened by the immunological method of Healfman et al., *Proc. Natl. Acad. Sci. USA* 80, 31-35 (1983), and colonies reacting positively with bFGF antibody are further characterized. The cells, following separation from their culture media, are lysed, and their supernatant obtained. Supernatent from these transformed cells is determined by RIA to be reactive with antibodies raised against bFGF.

100 ml. of cell supernatant is obtained, and the desired bFGF(24-68) fragment is purified as described above. Approximately 0.01 mg. of bFGF(24-68), purified to upwards of 98% by weight of total protein, is produced.

The biological activity of the synthetic bFGF fragment which contains the extraneous N-terminal methionine residue, is tested for biological activity with respect to ability to inhibit the growth of adult bovine aortic arch endothelial cells in culture, using an assay similar to that described in *J. Cell Biol.* 97, 1677-1685 (1983). Briefly, cells (at passage 3-10) are seeded at a density of $2 \times 10^3$ cells/dish on plastic tissue culture dishes and exposed to Dulbecco's modified Eagle's medium (DMEM) supplemented with 10% calf serum. Test samples, at a dilution ranging from $10^{-1}$ to $10^{-3}$, are added on day 0 and day 2 to the dishes. On day 4, triplicate dishes are trypsinized and counted in a Coulter counter. Background levels are ordinarily $10^5$ cells/dish, while those exposed to specified varying concentrations of the FGF antagonist contain as few as $10^4$ cells/dish. For a potency assay, a log response curve is established. For this purpose, 10 microliter-aliquots of a dilution (ranging from $10^{-1}$ to $10^{-5}$) of the original solution made in 0.5% bovine serum albumin (BSA)/D-MEM are added in triplicate.

The superfluous N-terminal residue is removable by partial chemical digestion with cyanogen bromide or phenyl isothiocyanate followed by treatment with a strong anhydrous acid, such as trifluoroacetic acid. After subjection to such cyanogen bromide treatment, the bFGF fragment continues to substantially reduce the total number of cells present per dish.

EXAMPLE XX

A plasmid, following amplification in one of the bFGF-fragment producing *E. Coli* clones of Example XIX, is isolated and cleaved with Eco RI and Sal I. This digested plasmid is electrophoresed on an agarose gel allowing for the separation and recovery of the amplified bFGF fragment insert. The insert is inserted into the plasmid pYEp, a shuttle vector which can be used to transform both *E. Coli* and *Saccharomyces cerevisiae* yeast. Insertion of the synthetic DNA chain at this point assures that the DNA sequence is under the control of a promoter, in proper reading frame from an ATG signal and properly spaced relative to a cap site. The shuttle vector is used to transform URA3, a strain of *S. cerevisiae* yeast from which the oratate monophophate decarboxylase gene is deleted.

The transformed yeast is grown in medium to attain log growth. The yeast is separated from its culture medium, and cell lysates are prepared. Pooled cell lysates are determined by RIA to be reactive with antibody raised against bFGF, demonstrating that a peptide containing bFGF peptide segments is expressed within the yeast cells.

The invention provides polypeptides which are biologically active antagonists of both basic FGF and acidic FGF, because both have been shown to act upon the same receptors, and should be available for biological and therapeutic use. The production of longer bFGF fragments can be carried out in both prokaryotic and eukaryotic cell lines. While such synthesis is easily demonstrated using either bacteria or yeast cell lines, the synthetic genes should be insertable for expression in cells of higher animals, such as mammalian tumor cells. Such mammalian cells may be grown, for example, as peritoneal tumors in host animals, and the desired bFGF fragments suitably harvested therefrom. The shorter bFGF fragments can simply be made by solid-phase or other coupling-type synthesis.

Although the above examples demonstrate that bFGF-fragments can be synthesized through recombinant DNA techniques, the examples do not purport to have maximized production. It is expected that subsequent selection of more efficient cloning vectors and host cell lines will increase the yield of bFGF fragments. Known gene amplification techniques for both eukaryotic and prokaryotic cells may be used to increase production. Secretion of the gene-encoded polypeptide from the host cell line into the culture medium is also considered to be an important factor in obtaining synthetic bFGF fragments in large quantities.

Brain and pituitary basic FGF preparations, as reported earlier, are mitogenic for a wide variety of normal diploid cultured cells derived from tissue originating from the primary or secondary mesenchyme, as well as from neuroectoderm. These include rabbit chondrocytes, bovine granulosa and adrenal cortex cells, bovine corneal endothelial cells, capillary endothelial cells derived from bovine adrenal cortex and human umbilical endothelial cells. FGF antagonists are useful biological materials for regulating in vitro growth of cultured cell lines and are expected to also function in this manner when administered in vivo locally and otherwise. Accordingly, FGF antagonist peptides have many potential therapeutic applications such as the treatment of vasoproliferative diseases of the eye, e.g. diabetic retinopathies, of proliferative diseases of the kidney, e.g. glomerulonephritis, of certain tumors, e.g. chondrosarcoma, and adrenal vascularization, as well as inhibiting neovascularization of solid tumors in formation, and of other similar infirmities.

Because it appears that the growth of human melanomas and other melanocytes is promoted by bFGF, the FGF antagonists should be effective to combat the growth of these cells and the growth promotion of certain related oncogenes, such as hst/KS3. More specifically, it is found that bFGF antagonists, in the presence of heparin, inhibit the response of melanocytes to the transforming oncogene protein KS3. It is expected that these peptides will also be antagonists to other of the FGF family of peptides, such as FGF-5.

Synthetic FGF antagonists or the nontoxic salts thereof, combined with a pharmaceutically acceptable carrier to form a pharmaceutical composition, may be administered to mammals, including humans, either intravenously, subcutaneously, intramuscularly or orally. The required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically-acceptable carrier.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, Thr can be substituted for Ser in what would be position 112 of the bFGF molecule, and Ser can be substituted for Pro in position 128, as these differences appear in the highly homologous human bFGF molecule. As also indicated hereinbefore, Met can be substituted for Trp in the 114-position, Phe can be substituted for Tyr in the 115-position, and Ala can be substituted for Ser in the 113-position. Other similar substitutions as would be obvious to one skilled in peptide chemistry may be made to provide equivalent FGF antagonists without departing from the scope of the invention. Extensions which do not change the FGF antagonist peptide into an FGF partial agonist having substantial agonist activity can be added to either or both termini, so long as they do not significantly lessen its biological potency as an FGF antagonist, and such polypeptides are considered to be equivalents of those disclosed. For example, the residue Tyr can be added at either terminus of a synthetic FGF antagonist without substantially affecting the biological potency of that particular antagonist. Inasmuch as the function of the peptide is primarily one of binding, it is the sequence that is most important, and the C-terminus can be free acid, amide or some equivalent moiety.

Specific features of the invention are emphasized in the claims which follow.

What is claimed is:

1. A peptide of the formula: H-Tyr-Cys-Lys-Asn-Gly-Gly-Phe-Phe-Leu-Arg-Ile-His-Pro-Asp-Gly-Arg-Val-Asp-$R_{42}$-Val-Arg-Glu-Lys-$R_{47}$-Asp-Pro-His-Ile-Lys-Leu-Gln-Leu-Gln-Ala-Glu-Glu-Arg-Gly-Val-Val-Ser-Ile-Lys-Gly-Val-Y, wherein Y is OH or $NH_2$, $R_{42}$ is Gly, Ala or Sar and $R_{47}$ is Ser, Ala or Thr or an N-terminally sequentially shortened fragment thereof or a C-terminally sequentially shortened fragment thereof or an N-terminally and C-terminally sequentially shortened fragment thereof, which fragment contains the sequence Pro-Asp-Gly-Arg.

2. A peptide according to claim 1 wherein twelve residues in sequence beginning at the N-terminus are deleted.

3. A peptide according to claim 1 wherein twenty-nine residues in sequence beginning at the C-terminus are deleted.

4. A peptide according to claim 2 wherein twenty-nine residues in sequence beginning at the C-terminus are deleted.

5. A peptide according to claim 1 wherein $R_{42}$ is Gly.

6. A peptide according to claim 5 wherein $R_{47}$ in Ser.

7. H-Tyr-Cys-Lys-Asn-Gly-Gly-Phe-Phe-Leu-Arg-Ile-His-Pro-Asp-Gly-Arg-Val-Asp-Gly-Val-Arg-Glu-Lys-Ser-Asp-Pro-His-Ile-Lys-Leu-Gln-Leu-Gln-Ala-Glu-Glu-Arg-Gly-Val-Val-Ser-Ile-Lys-Gly-Val-$NH_2$.

* * * * *

UNITED STATES PATENT AND TRADEMARK OFFICE
CERTIFICATE OF CORRECTION

PATENT NO. : 5,132,408
DATED : July 21, 1992
INVENTOR(S) : Baird, et al

Page 1 of 2

It is certified that error appears in the above-indentified patent and that said Letters Patent is hereby corrected as shown below:

On the title page, Item [22]:

November 14, 1988" insert --Related U.S. Application Data Continuation-in-Part of U.S. Ser. No. 854,843, Filed April 22, 1986--. Right-hand column, first line, correct the spelling of --Gospodarowicz--. Abstract, line 9, after "Another" insert --group--. Column 1, line 25, after "to" insert --be distinct--. Column 1, line 26, after "(1974)" insert a period (.). Column 1, line 28, after "either" delete "distinct". Column 1, line 30, after "another" insert --distinct--. Column 1, line 42, change "the" to --and--. Column 1, lines 42-43, delete "FGF has also been shown to substitute for epithelial cells." Column 6, line 28, change "pCRI," to --pCR1,--. Column 7, line 46, change "-Lys($X^7$-" to -- -Lys($X^7$)-Asn($X^8$)- --. Column 7, line 47, change "-His($X^9$-" to -- -His($X^9$)- --. Column 7, line 50, change "-Lys($X^7$-" to -- -Lys($X^7$)- --. Column 7, line 55, change "-Asn" (third occurrence) to -- -Asn($X^8$)- --. Column 9, line 63, change "-3,-" to -- -3'- --. Column 10, line 40, insert a period (.) after "BaSo$_4$)". Column 11, line 50, change "gly-" to -- -Gly- --. Column 11, line 50, change "-Arg($X^6$-" to -- -Arg($X^6$)- --.

UNITED STATES PATENT AND TRADEMARK OFFICE
CERTIFICATE OF CORRECTION

PATENT NO. : 5,132,408
DATED : July 21, 1992
INVENTOR(S) : Baird, et al

It is certified that error appears in the above-indentified patent and that said Letters Patent is hereby corrected as shown below:

Column 11, line 55, after "Tos" insert a comma. Column 11, line 59, insert a period (.) after "$CH_2Cl_2$". Column 12, line 9, change "$NH_{40}Ac$," to --$NH_4OAc$,--. Column 12, line 60, after "of" insert --[$Tyr^{50}$]--. Column 15, line 15, change "-bFGF(35-50-" to -- -bFGF(35-50)- --. Column 19, line 14, change "5," to --5'--. Column 19, line 20, change "4'" to --3'--. Column 19, line 25, change "$pUC_8$" to --pUC8--. Column 20, line 35, correct the spelling --monophosphate--.

Signed and Sealed this

Twenty-sixth Day of October, 1993

BRUCE LEHMAN

Attest:

Attesting Officer

Commissioner of Patents and Trademarks